United States Patent [19]

Freitag

[11] Patent Number: 5,741,296

[45] Date of Patent: Apr. 21, 1998

[54] INSTRUMENT FOR THE APPLICATION OF PROSTHESES INSIDE THE BODY

[75] Inventor: Lutz Freitag, Easen, Germany

[73] Assignee: Karl Storz GmbH & Co., Tuttlingen, Germany

[21] Appl. No.: 637,808

[22] PCT Filed: Oct. 28, 1994

[86] PCT No.: PCT/DE94/01269

§ 371 Date: Apr. 1, 1996

§ 102(e) Date: Apr. 1, 1996

[87] PCT Pub. No.: WO95/12356

PCT Pub. Date: May 11, 1995

[30] Foreign Application Priority Data

Nov. 2, 1993 [DE] Germany .......................... 43 37 370.4
May 26, 1994 [DE] Germany .......................... 44 18 449.2

[51] Int. Cl.$^6$ .................................................. A61B 17/00
[52] U.S. Cl. ............................ 606/205; 606/198; 623/1
[58] Field of Search ................................. 606/1, 108, 51, 606/52, 174, 191, 198, 205–211; 623/1, 12; 128/750–755; 294/99.2

[56] References Cited

U.S. PATENT DOCUMENTS

| 4,657,019 | 4/1987 | Walsh et al. ............................ 606/210 |
| 4,889,118 | 12/1989 | Schwiegerling ........................ 606/208 |
| 5,290,299 | 3/1994 | Fain et al. ................................ 606/207 |

FOREIGN PATENT DOCUMENTS

| 0099281 | 9/1898 | Germany ................................ 606/205 |
| 0339051 | 7/1921 | Germany ................................ 606/210 |
| 3812165 | 10/1989 | Germany . |
| 9109113 | 12/1991 | Germany . |
| 1205743 | 9/1970 | United Kingdom . |

*Primary Examiner*—William Lewis
*Attorney, Agent, or Firm*—Donald D. Mon

[57] ABSTRACT

An instrument for inserting a prosthesis into a body cavity and holding it in place. A shaft has a pair of pivoted jaws to open and close on the prosthesis. A releasable latch can hold the levers toward one another to exert a continuing grip on the prosthesis. A support element is slidably mounted to the shaft to hold the prosthesis in place after the jaws are opened and the shaft is withdrawn.

3 Claims, 1 Drawing Sheet

INSTRUMENT FOR THE APPLICATION OF PROSTHESES INSIDE THE BODY

TECHNICAL FIELD

The present invention relates to an instrument for the application of prostheses inside the body and, in particular, tracheobronchial prostheses.

BACKGROUND OF THE INVENTION

For the insertion of, by way of illustration, tracheobronchial prostheses hitherto two instruments were required: one, grasping tongs to grip the prosthesis and insert it into the tracheobronchial region; the other an auxiliary instrument for holding the prosthesis in the desired position during removal of the grasping tongs.

As the cross-section (lumen) at disposal is restricted, handling two instruments simultaneously often causes difficulties.

BRIEF DESCRIPTION OF THE INVENTION

The object of the present invention is to provide an instrument for the application of prostheses inside the body and, in particular tracheobronchial prostheses, permitting uncomplicated insertion of a prosthesis.

The present invention is based on the fundamental concept of providing an instrument having at least two moveable jaws, which in particular can be designed like known gripping tongs, with an additional sliding element which can be supported independently in the region into which the prosthesis is to be attached, thus by way of illustration to the tracheobronchial wall, during the removal of the tongs out of the tracheobronchial system. It is especially preferred if the operating elements of the jaws, which by way of illustration, can be designed like conventional handles of medical tongs, are provided with a detention device which permits securing the prosthesis without holding the handles. The detention of the handles will be releaseable, preferably by pressing a lever on the detention device.

BRIEF DESCRIPTION OF THE DRAWING

The present invention is made apparent in the following using a preferred embodiment with reference to the accompanying drawing showing in.

DESCRIPTION OF A PREFERRED EMBODIMENT

Figure 1:
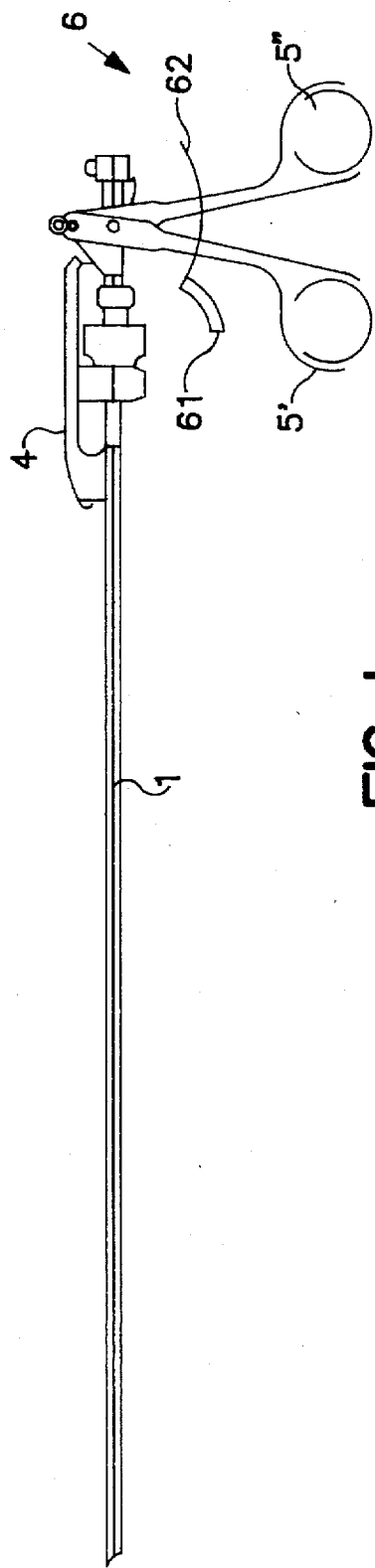
FIG. 1 a lateral view of the preferred embodiment of an instrument according to this invention.
Figure 2:
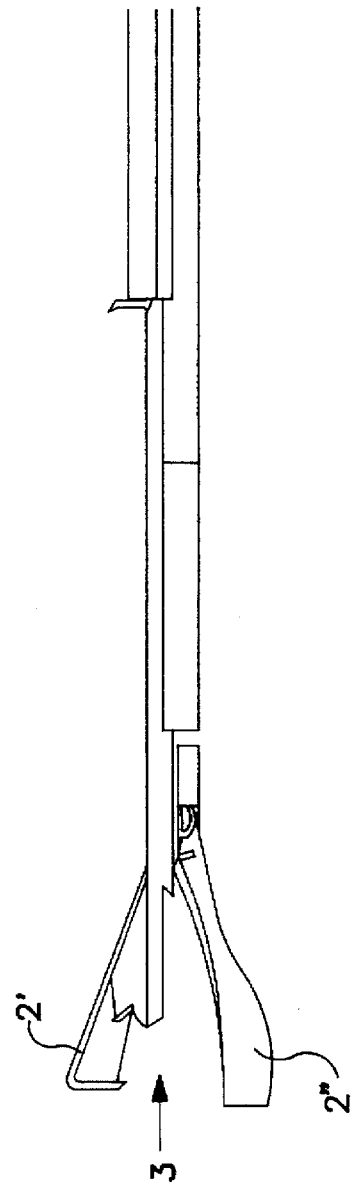
FIG. 2 is an enlarged view of the distal end of the instrument shown in FIG. 1.

The figures show an instrument for the application of prostheses inside a body and, in particular, for applying a tracheobronchial prostheses. The instrument is provided with an instrument shaft 1 bearing at its distal end two moveable jaws 2' and 2". The jaws 2' and 2" serve to hold a prosthesis (not shown), during the insertion procedure. Furthermore, a sliding element 3 is provided which can be slid along the instrument shaft 1 and which serves to hold the prosthesis in position during the removal of the instrument, for example from the tracheobronchial region.

Provided at the proximal end of the instrument shaft 1 are operating elements, to be explained in more detail hereinafter, for the jaws 2' and 2" and the sliding element 3:

Two handles 5' and 5" are hinged together to move the jaws. They are conventionally for medical tongs, and this case with finger loops. The handles 5' and 5" are provided with a detention device 6, which enables the prosthesis to continue to be held by the tongs without requiring continued attention by the surgeon. The detention device is provided, with a lever 62, which passes through the two handles 5' and 5" and by means of which detention is produced. Detention of the handles is released by pressing a lever 61 on the detention device 6.

The operating element of the sliding element 3 is a slide button 4 provided in the proximal end region of the instrument shaft 1. Furthermore, the sliding element at the distal end is provided with a V-shaped recess 31, which permits particularly efficient support for the prosthesis both while the jaws hold the prosthesis, and when the jaws are released and the gripping tongs are removed.

What is claimed is:

1. An instrument for inserting and holding a prosthesis in a body cavity comprising:

a shaft;

a pair of jaws mounted to said shaft, at least one of which jaws is movable relative to the other for closing and opening movement, respectively to grasp and to release a prosthesis;

a pair of handles mounted to said shaft, at least one of which is pivotally mounted and operatively connected to said jaws to cause said closing and opening movement respectively when brought toward one another or spread apart from one another;

releasable detention means so disposed and arranged as to latch said lever means together at a selected closed position to hold the prosthesis without maintaining a closure force on said lever means;

a sliding element slidably attached to said shaft, said sliding element having a spine extending adjacent to said shaft and a support element so disposed and arranged on said spine as be retractable from said jaws, and to be extendible beyond them, whereby a prosthesis held by the jaws may be engaged by the support while held by the jaws and inserted into the body and may remain in place to hold the prosthesis in position when the jaws release the prosthesis and the jaws and shaft are thereafter withdrawn from the body.

2. An instrument according to claim 1 in which said detention means is a latch.

3. An instrument according to claim 1 in which said support element includes a V-shaped notch for engagement with the prosthesis.

* * * * *